US009933389B2

(12) United States Patent
Higuchi et al.

(10) Patent No.: US 9,933,389 B2
(45) Date of Patent: *Apr. 3, 2018

(54) SENSOR CONTROL APPARATUS AND GAS DETECTION SYSTEM

(71) Applicant: NGK SPARK PLUG CO., LTD., Nagoya-shi, Aichi (JP)

(72) Inventors: Yuzo Higuchi, Komaki (JP); Tomonori Uemura, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 209 days.

This patent is subject to a terminal disclaimer.

(21) Appl. No.: 14/965,328

(22) Filed: Dec. 10, 2015

(65) Prior Publication Data

US 2016/0169832 A1    Jun. 16, 2016

(30) Foreign Application Priority Data

Dec. 12, 2014    (JP) .................................. 2014-251971

(51) Int. Cl.
*G01N 27/41*      (2006.01)
*G01N 27/419*     (2006.01)
*G01N 27/406*     (2006.01)

(52) U.S. Cl.
CPC ....... *G01N 27/419* (2013.01); *G01N 27/4065* (2013.01)

(58) Field of Classification Search
CPC ... G01N 27/4065; G01N 27/409; G01N 27/41
See application file for complete search history.

(56) References Cited

U.S. PATENT DOCUMENTS 6,553,817 B1 * 4/2003 Kotwicki .............. F01N 11/007
                                                       73/114.73

FOREIGN PATENT DOCUMENTS

JP        2008-008667 A      1/2008

OTHER PUBLICATIONS

JPO computer-generated English language translation of JP 2008-008667 A. Downloaded Sep. 1, 2017.*

* cited by examiner

*Primary Examiner* — Alexander S Noguerola
(74) *Attorney, Agent, or Firm* — Stites & Harbison, PLLC; Jeffrey A. Haeberlin; James R. Hayne (57) ABSTRACT

A sensor control apparatus of a gas detection system includes a digital computation section having a PID computation section, a first filter section, and a second filter section as functional sections. The first filter section digitally extracts a DAC control signal (first filter signal) from a digital signal representing a supply control current Tip computed by the PID computation section. The DAC control signal is a digital signal which represents the supply control current Tip for pump current and in which noise components superimposed as a result of digital computation in the PID computation section have been attenuated.

4 Claims, 4 Drawing Sheets

SENSOR CONTROL APPARATUS AND GAS DETECTION SYSTEM

CROSS REFERENCE TO RELATED APPLICATIONS

The present application claims priority from Japanese Patent Application No. 2014-251971, which was filed on Dec. 12, 2014, the disclosure of which is herein incorporated by reference in its entirety.

BACKGROUND OF THE INVENTION

Field of the Invention

The present invention relates to a sensor control apparatus for controlling a gas sensor which includes a detection cell for producing an electromotive force corresponding to a particular component contained in an object gas and an oxygen pump cell for performing pumping in or pumping out of oxygen in accordance with pump current, and to a gas detection system which includes the gas sensor and the sensor control apparatus.

Description of Related Art

There have been known a sensor control apparatus for controlling a gas sensor having a detection cell and an oxygen pump cell and a gas detection system which includes the gas sensor and the sensor control apparatus.

The detection cell of the gas sensor is a cell which produces an electromotive force corresponding to a particular component contained in an object gas, and the oxygen pump cell of the gas sensor is a cell which performs pumping in or pumping out of oxygen in accordance with pump current.

An example of such a gas sensor is an A/F sensor (oxygen sensor) which pumps in oxygen or pumps out oxygen contained in an object gas through use of an oxygen pump cell such that the electromotive force produced in a detection cell becomes equal to a target voltage set in advance and which linearly detects the concentration of oxygen contained in the object gas on the basis of the pump current flowing (supplied) to the oxygen pump cell at that time. Another example of such a gas sensor having an oxygen pump cell is an NOx sensor for detecting the concentration of NOx contained in an object gas.

Such a sensor control apparatus must have various computation functions for controlling the pump current of such a gas sensor, and must meet the demand for miniaturization of the apparatus. In view of these demands, a known sensor control apparatus employs a digital control section in place of an analog circuit for performing various controls (Patent Document 1).

Such a sensor control apparatus employing a digital control section includes analog-to-digital conversion sections (AD converters) which convert various analog signals detected from a gas sensor (for example, electromotive force produced in the detection cell) to digital values.

Another known sensor control apparatus is configured to switch a plurality of analog signals using a multiplexer to thereby allow conversion of analog signals to digital values even when the number of AD converters is smaller than the number of the analog signals.

In such a sensor control apparatus, the pump current of a gas sensor can be controlled by performing digital PID control while using various digital values converted from various analog signals (e.g., electromotive force produced in the detection cell of the gas sensor).

The above-mentioned digital control section can be rendered smaller in size as compared with an analog circuit. Also, when such a digital control section is used, an operation of changing control constants becomes easier as compared with the case where an analog circuit is used. Therefore, it becomes easier to adapt to control of gas sensors of a larger number of types and control of gas sensors having various characteristics.

RELATED ART DOCUMENTS

Patent Document 1 is Japanese Patent Application Laid-Open (kokai) No. 2008-008667.

BRIEF SUMMARY OF THE INVENTION

In gas detection performed through use of a gas sensor as described above, quicker response is demanded. However, in the case where the sampling rate of digital signals in a sensor control apparatus using a digital control section is increased in order to fulfil the demand for quicker response, the noise component (differential noise) produced as a result of digital PID control may increase.

Namely, in the case where the sampling rate of digital signals is increased so as to meet the demand for high-frequency response in sensor control, an internal computation value (gain) used in differential computation must be set to a larger value in order to cope with the increased sampling rate. As a result, differential noise in the digital signals may increase.

In view of the foregoing, an object of the present invention is to provide a sensor control apparatus and a gas detection system which can suppress an increase in the level of noise components even when the sampling rate of digital signals is increased.

A sensor control apparatus according to a first aspect of the present invention is a sensor control apparatus for controlling a gas sensor having a detection cell and an oxygen pump cell, and includes an analog-to-digital conversion section, a supply control value computation section, a digital-to-analog conversion section, a first filter section, and a second filter section.

The detection cell of the gas sensor is a cell which produces an electromotive force corresponding to a particular component contained in an object gas, and the oxygen pump of the gas sensor is a cell which performs pumping in or pumping out of oxygen in accordance with a pump current.

The analog-to-digital conversion section converts (is configured to convert) an analog signal representing the electromotive force of the detection cell to a digital value of the electromotive force.

The supply control value computation section digitally computes (is configured to digitally compute) a value for controlling the supply of the pump current supplied to the oxygen pump cell (hereinafter, the value will be referred to as the "supply control value for the pump current") on the basis of the digital value of the electromotive force. The digital-to-analog conversion section generates the pump current supplied to the oxygen pump cell on the basis of a digital signal representing the supply control value for the pump current.

The first filter section digitally extracts (is configured to digitally extract) a first filter signal from a digital signal representing the supply control value for the pump current such that components of the digital signal whose frequencies are higher than a predetermined first cut-off frequency are attenuated. The second filter section digitally extracts (is configured to digitally extract) a second filter signal from the first filter signal, extracted by the first filter section, such that components of the first filter signal whose frequencies are higher than a predetermined second cut-off frequency are attenuated.

The digital-to-analog conversion section generates the pump current on the basis of the first filter signal. The second filter section outputs the second filter signal to an external apparatus or section (for example, a particular component computation section for computing the concentration of the particular component contained in the object gas using the pump current signal) as a pump current signal for detection of the particular component contained in the object gas.

Since the first filter signal is a signal obtained from the digital signal representing the supply control value for the pump current such that components (noise components) of the digital signal whose frequencies are higher than the first cut-off frequency are attenuated, the first filter signal is a digital signal which represents the supply control value for the pump current and in which the noise components superimposed as a result of the digital computation in the supply control value computation section have been attenuated. Therefore, even in the case where the sampling rate of the digital signal is increased, an increase in the level of the differential noise component of the digital signal can be suppressed.

Since the second filter signal is a signal obtained from the first filter signal such that components (noise components) whose frequencies are higher than the second cut-off frequency are attenuated, the second filter signal is a digital signal in which the noise components (noise components superimposed as a result of the digital computation in the supply control value computation section) have been further attenuated or removed from the first filter signal.

Since the first filter signal is smaller in the number of times of filter processing as compared with the second filter signal, the first filter signal is a digital signal which represents the supply control value for the pump current and which reflects, to a relatively great extent, the latest change in the electromotive force of the detection cell. Such a digital signal is suitable for feedback control of the oxygen pump cell. Therefore, by supplying to the oxygen pump cell the pump current generated on the basis of the first filter signal, the pumping (pumping out and pumping in) of oxygen by the oxygen pump cell can be performed properly in accordance with the latest change in the electromotive force of the detection cell.

Since the second filter signal is larger in the number of times of filter processing as compared with the first filter signal, the second filter signal is a digital signal which represents the supply control value for the pump current and which reflects, to a relatively great extent, a change in the electromotive force of the detection cell over a long period of time. Such a digital signal is suitable for detection of a particular component contained in the object gas. Therefore, by using the second filter signal as a signal for detecting the particular component contained in the object gas, it becomes possible to detect the particular component contained in the object gas on the basis of a change in the electromotive force of the detection cell over a long period of time.

As a result, for example, in the case where the particular component computation section, which computes the concentration of the particular component contained in the object gas using the pump current signal, receives the second filter signal from the second filter section, the accuracy in computing the concentration of the particular component in the particular component computation section can be improved, whereby the accuracy in detecting the particular component contained in the object gas can be improved.

Therefore, according to the sensor control apparatus of the present invention, even when the sampling rate of the digital signal is increased, an increase in the level of noise components can be suppressed. Also, according to the sensor control apparatus of the present invention, pumping of oxygen by the oxygen pump cell can be performed properly, and the accuracy in detecting the particular component contained in the object gas can be improved.

Notably, since the above-described effect is obtained when the second filter signal is larger in the number of times of filter processing as compared with the first filter signal, the first cut-off frequency may be equal to the second cut-off frequency, or the first cut-off frequency may be higher than the second cut-off frequency.

In the above-described sensor control apparatus, the first cut-off frequency may be higher than the second cut-off frequency.

In this case, the first filter signal becomes a digital signal which contains components within a wider frequency range as compared with the second filter signal and becomes a digital signal which represents the supply control value for the pump current and which reflects, to a relatively great extent, the latest change in the electromotive force of the detection cell. Therefore, by supplying to the oxygen pump cell the pump current generated on the basis of the first filter signal, the pumping of oxygen by the oxygen pump cell can be performed properly in accordance with the latest change in the electromotive force of the detection cell.

Also, the second filter signal becomes a digital signal which contains components within a narrower frequency range as compared with the first filter signal and becomes a digital signal which represents the supply control value for the pump current and which reflects, to a relatively great extent, a change in the electromotive force of the detection cell over a long period of time. Therefore, by using the second filter signal as a signal for detecting the particular component contained in the object gas, the particular component contained in the object gas can be detected on the basis of a change in the electromotive force of the detection cell over a long period of time. As a result, the accuracy in detecting the particular component can be improved.

The above-described sensor control apparatus may include a multiplexer to which a plurality of analog signals, including at least the electromotive force of the detection cell, are input and which outputs the plurality of analog signals one by one in a predetermined order.

Notably, the analog-to-digital conversion section converts the analog signals output from the multiplexer to digital values.

When the multiplexer outputs the plurality of analog signals one by one in the predetermined order, the multiplexer classifies each of them as a high occurrence-frequency signal or a low occurrence-frequency signal. The high occurrence-frequency signal is output two or more times in an all signal output period during which all the analog signals are output. The low occurrence-frequency signal is output once in the signal output period. The analog signal(s) classified as the high occurrence-frequency signal includes at least the electromotive force of the detection cell.

Namely, the multiplexer in this sensor control apparatus can increase the sampling frequency of the high occurrence-frequency signal by outputting the analog signals while classifying each of them as a high occurrence-frequency signal which is high in output frequency or a low occurrence-frequency signal which is low in output frequency, instead of outputting all the plurality of analog signals at the same frequency.

Since the analog signal(s) classified as the high occurrence-frequency signal includes at least the electromotive force of the detection cell, the sampling frequency of the electromotive force of the detection cell can be increased without a requirement to enhance the performance of the analog-to-digital conversion section (AD converter).

Therefore, the sensor control apparatus of the present invention can increase the sampling frequency in the AD conversion (to a digital value) of the analog signal regarding the electromotive force of the detection cell detected from the gas sensor, while suppressing an increase in the cost of the analog-to-digital conversion section.

In the sensor control apparatus including the above-described multiplexer, the multiplexer may output the electromotive force of the detection cell as the high occurrence-frequency signal at constant intervals.

Since the electromotive force of the detection cell is output as the high occurrence-frequency signal at constant intervals, as compared with the case where the electromotive force of the detection cell is output at irregular timings, the computation processing in the supply control value computation section (e.g., processing of computing the supply control value based on the electromotive force of the detection cell) can be simplified, and the supply control value can be computed quickly.

Therefore, according to this sensor control apparatus, the supply control value can be computed quickly, and a quick response can be realized in the gas detection performed through use of the gas sensor.

In the sensor control apparatus including the above-described multiplexer, the analog signal(s) classified as the low occurrence-frequency signal may include a signal regarding a potential difference between a reference potential of the sensor control apparatus and the potential of at least one electrode terminal selected from two electrode terminals of the oxygen pump cell and two electrode terminals of the detection cell.

Namely, since the analog signal(s) classified as the low occurrence-frequency signal includes a signal regarding the potential difference between the reference potential of the sensor control apparatus and the potential of at least one electrode terminal selected from the two electrode terminals of the oxygen pump cell and the two electrode terminals of the detection cell, the sensor control apparatus can obtain, through the analog-to-digital conversion section, an analog signal representing the above-described potential difference, among the plurality of analog signals, although the frequency of occurrence is lower than that of the high occurrence-frequency signal (the electromotive force of the detection cell).

As a result, the sensor control apparatus can perform various operations using the analog signal representing the above-described potential difference, which is the low occurrence-frequency signal, even in a state in which the sampling frequency in the AD conversion of the analog signal representing the electromotive force of the detection cell is increased. Examples of the operations include detecting anomalous states of at least one electrode terminal of the electrode terminals of the oxygen pump cell and the detection cell (short-to-power potential anomaly, short-to-reference potential anomaly, wire breakage anomaly, etc. of the electrode terminal), and outputting the analog signal representing the above-described potential difference to an external apparatus.

Notably, it is sufficient that the analog signal(s) classified as the low occurrence-frequency signal includes the signal regarding the potential difference between the reference potential of the sensor control apparatus and the potential of at least one of the two electrode terminals of the oxygen pump cell and the two electrode terminals of the detection cell. Namely, the low occurrence-frequency signal may be a single signal regarding the potential difference between the reference potential of the sensor control apparatus and the potential of a particular one of the electrode terminals of the oxygen pump cell and the detection cell, or may be each of a plurality of signals regarding the potential differences between the reference potential of the sensor control apparatus and the potentials of all the electrode terminals of the oxygen pump cell and the detection cell.

However, in the case where a plurality of signals are output as the low occurrence-frequency signal, the signals (low occurrence-frequency signals) are output from the multiplexer one by one in a predetermined order and in consideration of the output order of the high occurrence-frequency signal.

A gas detection system according to another aspect of the present invention is a gas detection system which comprises a gas sensor including a detection cell and an oxygen pump cell, and a sensor control apparatus for controlling the gas sensor, wherein the sensor control apparatus is the above-described sensor control apparatus.

The detection cell of the gas sensor is a cell which produces an electromotive force corresponding to a particular component contained in an object gas, and the oxygen pump of the gas sensor is a cell which performs pumping in or pumping out of oxygen in accordance with pump current.

Since the gas detection system includes the above-described sensor control apparatus, the gas detection system can suppress an increase in the level of noise components even when the sampling rate of the digital signal is increased, as in the case of the above-described sensor control apparatus.

The sensor control apparatus and the gas detection system of the present invention can suppress an increase in the level of noise components even when the sampling rate of the digital signal is increased.

BRIEF DESCRIPTION OF THE DRAWINGS

Illustrative aspects of the invention will be described in detail with reference to the following figures wherein.

DETAILED DESCRIPTION OF EXEMPLARY EMBODIMENTS OF THE INVENTION

Embodiments to which the present invention is applied will be described with reference to the drawings.

Notably, needless to say, the present invention is not limited to the following embodiments, and various forms may be employed so long as they fall within the technical scope of the present invention.

A. First Embodiment

1-1. Overall Configuration

Figure 1:
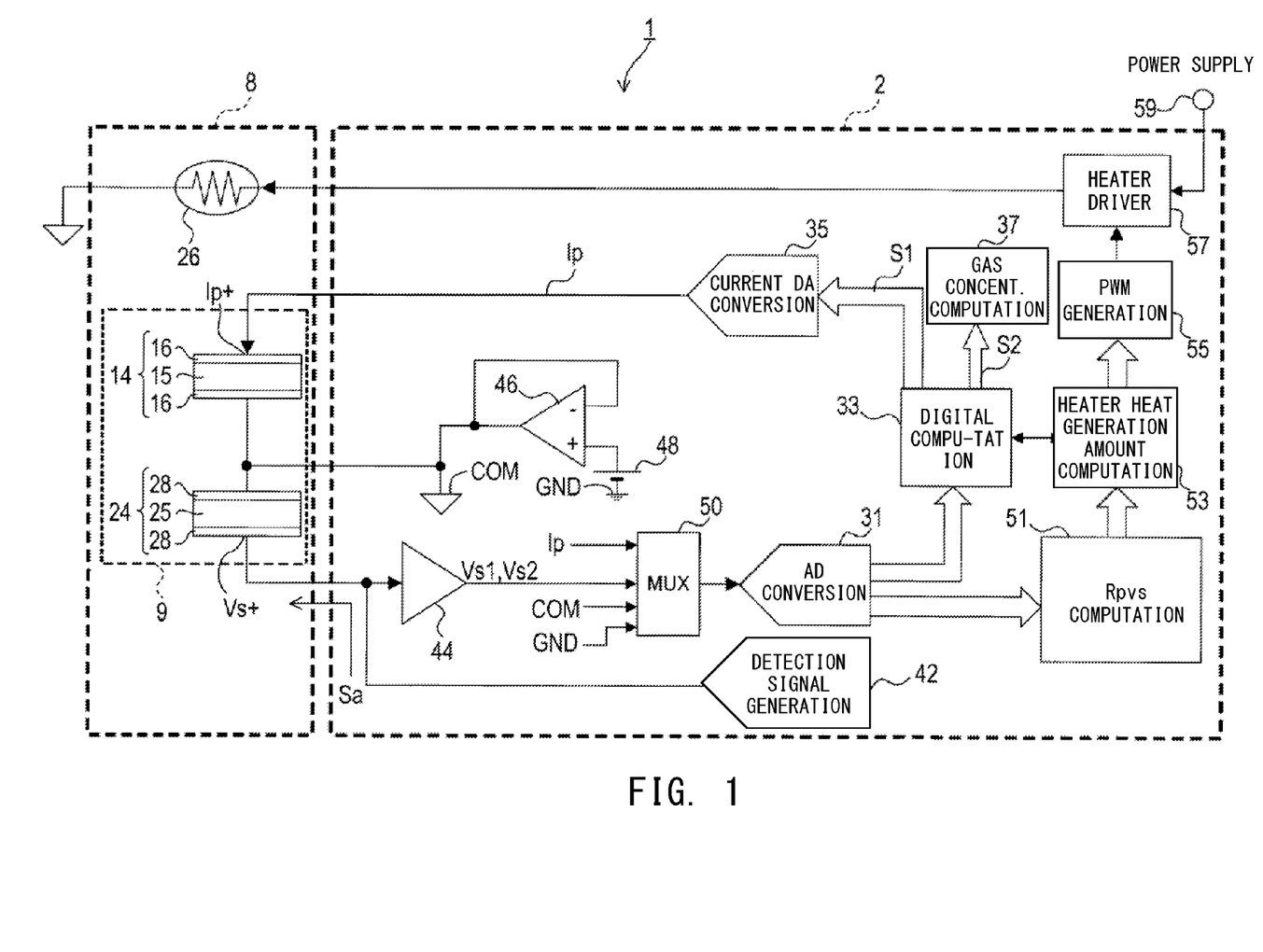
FIG. 1 is an overall diagram of a gas detection system.

FIG. 1 is an overall diagram of a gas detection system 1 according to an embodiment of the present invention.

The gas detection system 1 is used, for example, for the purpose of detecting a particular gas (oxygen in the present embodiment) contained in exhaust gas discharged from an internal combustion engine.

The gas detection system 1 includes a gas sensor 8 for detecting oxygen and a sensor control apparatus 2 for controlling the gas sensor 8. The gas detection system 1 reports the detected oxygen concentration to an engine control apparatus (not shown).

The engine control apparatus is a microcontroller which executes various types of control processing for controlling the internal combustion engine. As one of the various types of control processing, the engine control apparatus executes air-fuel ratio control for the internal combustion engine while using the oxygen concentration detected by the gas detection system 1.

The gas sensor 8 is provided on an exhaust pipe of the internal combustion engine (engine) and is used to detect the concentration of oxygen contained in exhaust gas in a width range. The gas sensor 8 is also called a linear lambda sensor. The gas sensor 8 is composed of a sensor element 9 and a heater 26.

The sensor element 9 is composed of a pump cell 14 and an electromotive force cell 24.

The pump cell 14 includes an oxygen-ion-conducting solid electrolyte body 15 formed of partially-stabilized zirconia ($ZrO_2$), and a pair of porous electrodes 16 mainly formed of platinum and provided on the front and back surfaces of the solid electrolyte body 15. The electromotive force cell 24 includes an oxygen-ion-conducting solid electrolyte body 25 formed of partially-stabilized zirconia ($ZrO_2$), and a pair of porous electrodes 28 mainly formed of platinum and provided on the front and back surfaces of the solid electrolyte body 25.

The heater 26 is composed of a heating resistor which produces heat when externally energized. The heater 26 is provided in order to heat the pump cell 14 and the electromotive force cell 24, thereby bringing them into an activated state.

Notably, the gas sensor 8 includes a measurement chamber (not shown) between the pump cell 14 and the electromotive force cell 24 in such a manner that the measurement chamber is located inside the gas sensor 8. An object gas (exhaust gas in the present embodiment) is introduced into the measurement chamber through a porous diffusion layer (not shown).

By use of the electromotive force cell 24, the gas sensor 8 generates an electromotive force (detection voltage Vs) corresponding to the oxygen concentration in the measurement chamber (in other words, the oxygen concentration of the object gas introduced into the measurement chamber through the porous diffusion layer). Specifically, the electromotive force cell 24 generates a detection voltage Vs corresponding to the difference in oxygen concentration between the front and back porous electrodes 28 of the electromotive force cell 24. Namely, the detection voltage Vs output from the electromotive force cell 24 changes with the oxygen concentration in the measurement chamber.

By use of the pump cell 14, the gas sensor 8 pumps out the oxygen contained in the object gas within the measurement chamber and pumps oxygen into the measurement chamber such that the detection voltage Vs from the electromotive force cell 24 becomes equal to a predetermined reference value (e.g., 450 mV). Specifically, a pump current Ip is caused to flow between the front and back porous electrodes 16 of the pump cell 14 so as to pump oxygen from the measurement chamber and pump oxygen into the measurement chamber, thereby adjusting the oxygen concentration in the measurement chamber.

Namely, the gas sensor 8 is used to detect the concentration of oxygen contained in the object gas on the basis of the pump current Ip applied to the pump cell 14 such that the oxygen concentration in the measurement chamber becomes equal to the predetermined target concentration (e.g., an oxygen concentration corresponding to the stoichiometric air-fuel ratio).

The sensor control apparatus 2 detects the oxygen concentration of the exhaust gas by driving and controlling the gas sensor 8, and notifies the engine control apparatus (not shown) of the detected oxygen concentration.

The sensor control apparatus 2 includes an AD conversion section 31 (analog-to-digital conversion section 31), a digital computation section 33, a current DA conversion section 35 (current digital-to-analog conversion section 35), a gas concentration computation section 37, a detection signal generation section 42, a buffer 44, an operational amplifier 46, a reference voltage generation section 48, a multiplexer 50, an Rpvs computation section 51, a heater heat generation amount computation section 53, a PWM generation section 55, and a heater driver 57.

The detection signal generation section 42 inputs to the electromotive force cell 24 of the gas sensor 8 an impedance detection signal Sa for detecting the internal resistance of the electromotive force cell 24 of the gas sensor 8. Specifically, the detection signal generation section 42 supplies a constant current to the electromotive force cell 24 as the impedance detection signal Sa in response to an instruction from the digital computation section 33.

The buffer 44 detects the voltage between the opposite ends of the electromotive force cell 24 at high impedance, and outputs it to the multiplexer 50 at low impedance. Notably, when the impedance detection signal Sa is not input, the voltage between the opposite ends of the electromotive force cell 24 becomes a sensor output signal Vs1 (detection voltage Vs) which changes with the oxygen concentration in the measurement chamber. In contrast, when the impedance detection signal Sa is input, the voltage between the opposite ends of the electromotive force cell 24 becomes a response signal Vs2 which changes with the internal resistance of the electromotive force cell 24.

The operational amplifier 46 sets the potential of a common terminal COM, to which the pump cell 14 and the electromotive force cell 24 are connected, to a predetermined potential. Specifically, the operational amplifier 46 sets the potential of the common terminal COM to a potential which is determined on the basis of the output voltage (2.5 V in the present embodiment) of the reference voltage generation section 48 with the ground potential GND used as a reference. Notably, in the present embodiment, the ground potential GND corresponds to the reference potential of the sensor control apparatus 2.

The multiplexer 50 receives a plurality of analog signals and outputs the plurality of analog signals one by one in a predetermined order.

In the present embodiment, the plurality of analog signals input to the multiplexer 50 includes "voltage between the Vs+ terminal of the electromotive force cell 24 and the common terminal COM" (Vs+-COM voltage), "voltage between the Ip+ terminal of the pump cell 14 and the ground potential GND" (Ip+-GND voltage), "voltage between the common terminal COM and the ground potential GND" (COM-GND voltage), and "voltage between the Vs+ terminal of the electromotive force cell 24 and the ground potential GND (Vs+-GND voltage). Notably, the Vs+ terminal and the common terminal COM correspond to the two electrode terminals of the electromotive force cell 24, and the Ip+ terminal and the common terminal COM correspond to the two electrode terminals of the pump cell 14.

The multiplexer 50 (hereinafter also referred to as the MUX 50) outputs one of the plurality of received analog signals to the AD conversion section 31. The multiplexer 50 determines which one of the analog signals is to be output on the basis of an instruction from the digital computation section 33.

The multiplexer 50 includes a plurality of changeover switch sections (not shown) disposed on connection paths between a plurality of input terminals and a single output terminal. The states (ON/OFF states) of the plurality of changeover switch sections are set on the basis of the instruction from the digital computation section 33, whereby the multiplexer 50 can output one of the plurality of received analog signals.

The AD conversion section 31 converts the analog signal output from the multiplexer 50 to a digital value, and informs the digital computation section 33 and the Rpvs computation section 51 of the digital value.

The digital computation section 33 performs computation control processing, such as sensor control processing and pump current control processing; signal switching control processing for controlling the operation of the multiplexer 50; etc. The signal switching control processing and the pump current control processing will be described later.

The sensor control apparatus 2 includes an unillustrated EEPROM and an unillustrated RAM.

The EEPROM is a storage section which stores the contents of the computation control processing, various parameters used for the computation control processing, and others. In addition, the EEPROM stores various pieces of information (the maximum permissible current of the pump cell 14, etc.) which are determined in accordance with the type and characteristics of the gas sensor 8, which is a controlled object. These pieces of information are stored in the EEPROM during the fabrication of the sensor control apparatus 2.

The RAM is a storage section which temporarily stores control data, etc. used for various kinds of computation control processing.

The current DA conversion section 35 performs DA conversion on the basis of the DAC control signal S1 which contains information of a supply control value for the pump current Ip computed by the digital computation section 33 and supplies the pump current Ip to the pump cell 14.

The current DA conversion section 35 receives the DAC control signal S1 which contains information (supply direction and current value) of the supply control value for the pump current Ip computed by the digital computation section 33, and performs DA conversion on the basis of the received digital information, and supplies to the pump cell 14 a pump current determined on the basis of the DAC control signal S1.

The gas concentration computation section 37 computes the concentration of a particular gas (oxygen in the present embodiment) contained in exhaust gas on the basis of the gas detection signal S2 which contains information of the supply control value for the pump current Ip computed by the digital computation section 33.

Namely, the gas concentration computation section 37 computes the concentration of oxygen contained in the object gas on the basis of the pump current Ip supplied to the pump cell 14 such that the oxygen concentration in the measurement chamber becomes equal to the predetermined target concentration (e.g., an oxygen concentration corresponding to the stoichiometric air-fuel ratio).

The Rpvs computation section 51 computes the internal resistance Rpvs of the electromotive force cell 24 on the basis of the response signal Vs2 and the sensor output signal Vs1 notified from the AD conversion section 31.

The heater heat generation amount computation section 53 digitally computes the temperature of the gas sensor 8 on the basis of the internal resistance Rpvs computed by the Rpvs computation section 51, and computes a heater heat generation amount which is necessary to make the computed temperature approach the sensor target temperature or maintain the computed temperature at the sensor target temperature.

The PWM signal generation section 55 computes the duty ratio of the power supplied to the heater 26 on the basis of the heater heat generation amount computed by the heater heat generation amount computation section 53, and generates a PWM control signal corresponding to the duty ratio.

By use of the power supplied from a power supply apparatus 59, the heater driver 57 energizes the heater 26, while controlling the energization on the basis of the PWM control signal received from the PWM signal generation section 55. Thus, the heater 26 produces heat which is necessary to make the temperature of the gas sensor 8 approach the sensor target temperature or maintain the temperature of the gas sensor 8 at the sensor target temperature.

1-2. Signal Switching Control Processing

Of various types of control processing executed by the digital computation section 33, the signal switching control processing for controlling the operation of the multiplexer 50 will be described.

In the signal switching control processing, the digital computation section 33 controls the operation of the multiplexer 50 such that the four analog signals input to the multiplexer 50 are output one by one in a predetermined order.

Figure 2:
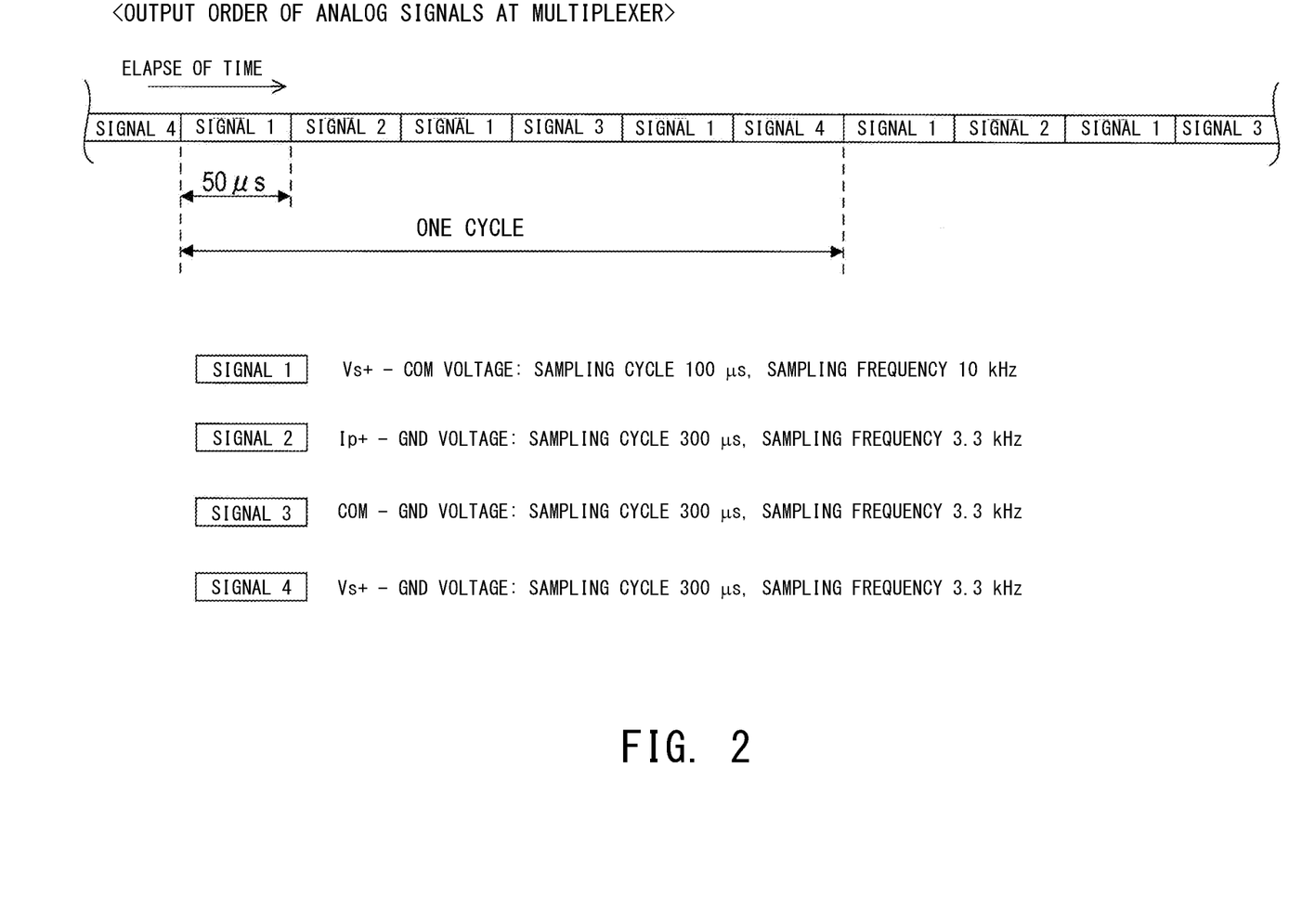
FIG. 2 is an illustration showing the output order of analog signals at a multiplexer.

In the present embodiment, the digital computation section 33, which executes the signal switching control processing, controls the operation of the multiplexer 50 such that the analog signal of the Vs+-COM voltage (signal 1), the analog signal of the Ip+-GND voltage (signal 2), the analog signal of the COM-GND voltage (signal 3), and the analog signal of the Vs+-GND voltage (signal 4) are output in the order shown in FIG. 2.

Namely, the multiplexer 50 having received the instruction from the digital computation section 33 outputs the analog signals in the order of, for example, "signal 1, signal 2, signal 1, signal 3, signal 1, signal 4." Also, the multiplexer 50 having received the instruction from the digital computation section 33 repeatedly outputs the plurality of analog signals while regarding, as one cycle, the period of output of "signal 1, signal 2, signal 1, signal 3, signal 1, signal 4." Notably, the output period of a single signal is 50 μs and one cycle is 300 μs.

Since the multiplexer 50 outputs the four analog signals in such an order, whereas signal 1 is output two or more times during the all signal output period (one cycle) during which all the analog signals are output, each of signal 2 to signal 4 is output once in one cycle.

As described above, the signal switching control processing controls the operation of the multiplexer 50 so as to output the plurality of analog signals while classifying each of them as a high occurrence-frequency signal which is output two or more times in each cycle or a low occurrence-frequency signal which is output once in each cycle.

Notably, instead of outputting all the plurality of analog signals at the same frequency, the multiplexer 50 outputs the analog signals while classifying each of them as a high occurrence-frequency signal which is high in output frequency or a low occurrence-frequency signal which is low in output frequency. As a result, the sampling frequency of signal 1 (the analog signal of the Vs+-COM voltage) which is a high occurrence-frequency signal can be increased.

Signal 1 (the analog signal of the Vs+-COM voltage) is an analog signal representing the electromotive force of the electromotive force cell 24.

Therefore, the sensor control apparatus 2 can increase the sampling frequency of the electromotive force of the electromotive force cell 24, without a requirement to enhance the performance of the AD conversion section 31, as compared with a configuration including a multiplexer which outputs signal 1 to signal 4 at the same frequency.

Figure 4:
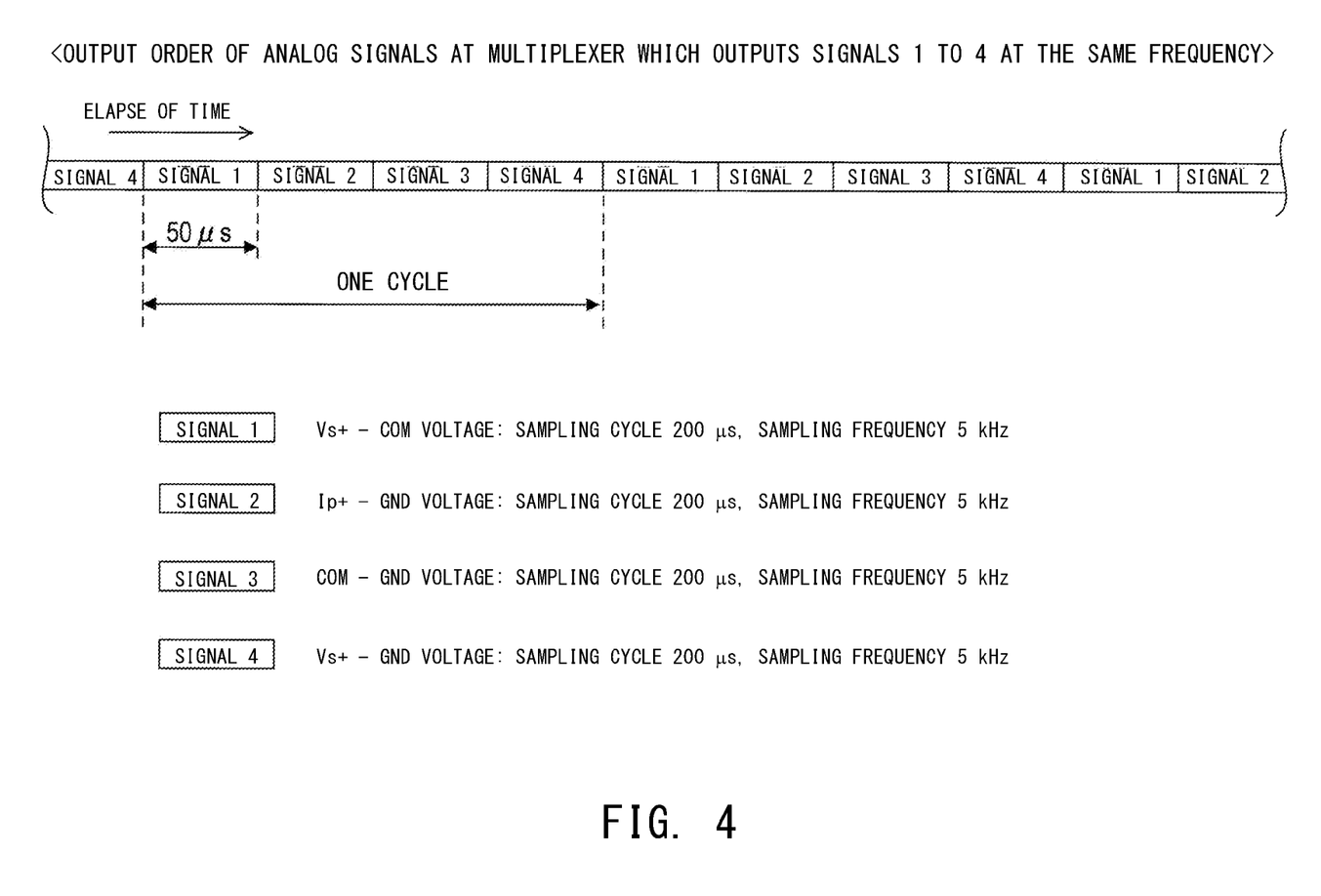
FIG. 4 is an illustration showing the output order of analog signals at a multiplexer which outputs signal 1 to signal 4 at the same frequency.

FIG. 4 shows an illustration representing the output order of the analog signals at a multiplexer which outputs signal 1 to signal 4 at the same frequency.

The sampling cycle and sampling frequency of each of analog signals (signals 1 to 4) output in the order shown in FIG. 4 are 200 µs and 5 kHz, respectively.

In contrast, the analog signals (signals 1 to 4) output from the multiplexer 50 of the present embodiment have sampling cycles and sampling frequencies as shown in FIG. 2. Specifically, the sampling cycle and sampling frequency of signal 1 are 100 µs and 10 kHz, respectively, and the sampling cycles and sampling frequencies of signals 2 to 4 are 300 µs and 3.3 kHz, respectively.

As a result, the multiplexer 50 of the present embodiment can increase the sampling frequency of signal 1 from 5 kHz to 10 kHz, as compared with the multiplexer which outputs signal 1 to signal 4 at the same frequency.

The low occurrence-frequency signals output from the multiplexer 50 are signal 2, signal 3, and signal 4.

Signal 2 is the analog signal of the Ip+-GND voltage (specifically, the potential difference between the potential of the Ip+ terminal and the ground potential GND (the reference potential)) and is an analog signal which represents the potential of an end portion of the pump cell 14 which is connected to the current DA conversion section 35. Signal 3 is the analog signal of the COM-GND voltage (specifically, the potential difference between the potential of the common terminal COM and the ground potential GND (the reference potential)) and is an analog signal representing the potential of the common terminal COM. Signal 4 is the analog signal of the Vs+-GND voltage (specifically, the potential difference between the potential of the Vs+ terminal and the ground potential GND (the reference potential)) and is an analog signal representing the potential of an end portion of the electromotive force cell 24 which is connected to the buffer 44.

Namely, the analog signals representing the potential differences between the reference potential of the sensor control apparatus 2 (GND potential) and the potentials of the electrode terminals (the Ip+ terminal, the COM terminal, and the Vs+ terminal) of the pump cell 14 and the electromotive force cell 24 are contained in the low occurrence-frequency signals. Therefore, the sensor control apparatus 2 can obtain the analog signals (signals 2, 3, and 4) representing the above-described potential differences, among the plurality of the analog signals, through the AD conversion section 31, although the frequencies of these analog signals are lower than that of the high occurrence-frequency signal (the electromotive force of the electromotive force cell 24).

As a result, these analog signals (signals 2, 3, and 4) which are low occurrence-frequency signals and represent the above-described potential differences allow the sensor control apparatus 2 to detect anomalous states (short-to-power potential anomaly, short-to-reference potential anomaly, wire breakage anomaly, etc.) of the electrode terminals (the Ip+ terminal, the COM terminal, and the Vs+ terminal) of the pump cell 14 and the electromotive force cell 24 by use of the digital computation section 33 or other devices. Also, the sensor control apparatus 2 can output these analog signals (signals 2, 3, and 4) to an external apparatus.

Also, as can be understood from FIG. 2, the multiplexer 50 always outputs signal 1 (the analog signal of the Vs+-COM voltage) at constant intervals not only within the period of a single cycle but also within a period including a plurality of cycles.

Since signal 1 (the electromotive force of the electromotive force cell 24) is output at constant intervals, as compared with the case where signal 1 (the electromotive force of the electromotive force cell 24) is output at irregular timings, the computation processing in the digital computation section 33 (e.g., processing of computing the supply control value for the pump current Ip based on the electromotive force of the electromotive force cell 24) can be simplified, and the supply control value can be computed quickly.

1-3. Pump Current Control Processing

Next, of the various types of control processing executed by the digital computation section 33, the pump current control processing will be described.

The pump current control processing is computation control processing for controlling the pump current Ip supplied to the pump cell 14 such that the detection voltage Vs of the electromotive force cell 24 becomes equal to the target control voltage (for example, 450 mV in the present embodiment).

Figure 3:
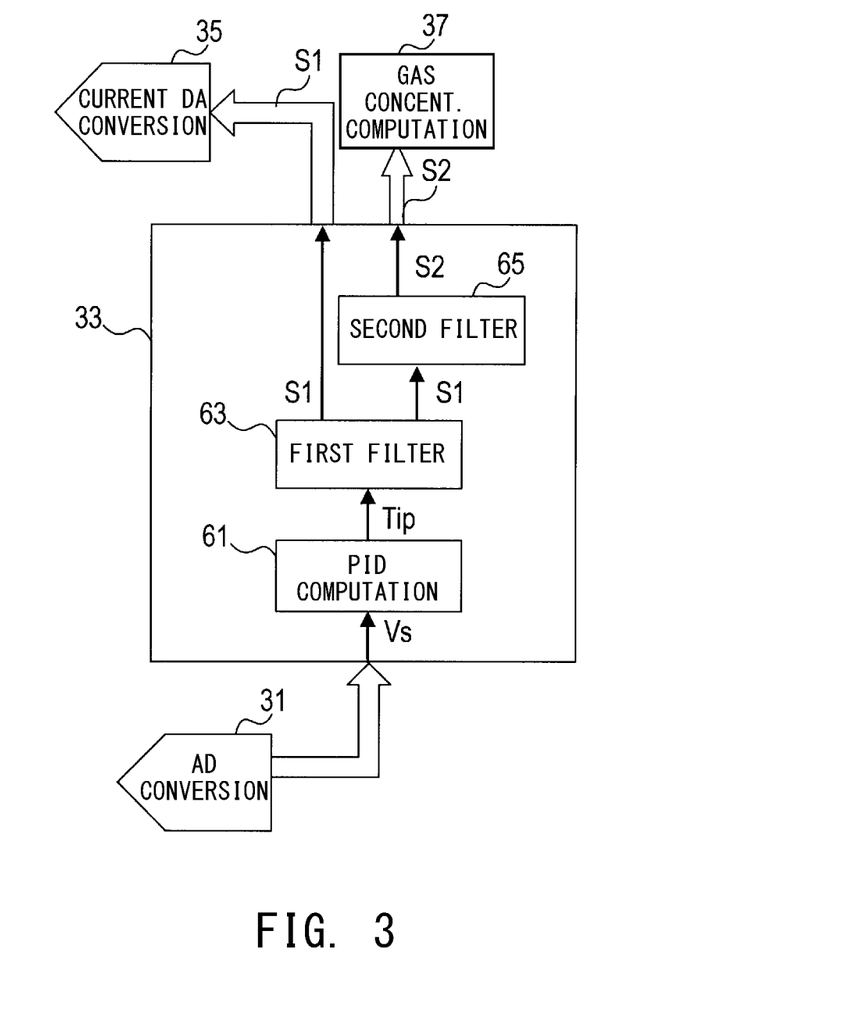
FIG. 3 is a functional block diagram of a digital computation section at the time when the digital computation section executes pump current control processing.

FIG. 3 shows a functional block diagram of the digital computation section 33 at the time when the digital computation section executes the pump current control processing.

The digital computation section 33 at the time when it executes the pump current control processing includes a PID computation section 61, a first filter section 63, and a second filter section 65 as functional sections.

The PID computation section 61 performs PID computation on the basis of the deviation ΔVs between the target control voltage (450 mV) and the detection voltage Vs of the electromotive force cell 24 (the electromotive force of the electromotive force cell 24), and computes the supply control value (supply control current Tip) for the pump current Ip supplied to the pump cell 14 such that the deviation ΔVs approaches 0 (in other words, the detection voltage Vs approaches the target control voltage).

The first filter section 63 digitally extracts a DAC control signal S1 (first filter signal S1) from a digital signal representing the supply control current Tip, computed by the PID computation section 61, such that components of the digital signal whose frequencies are higher than a predetermined first cut-off frequency (100 Hz in the present embodiment) are attenuated.

Since the DAC control signal S1 is a signal obtained from the digital signal representing the supply control current Tip for the pump current Ip such that components (noise components) of the digital signal whose frequencies are higher than the first cut-off frequency are attenuated, the DAC control signal S1 is a digital signal which represents the supply control current Tip for the pump current Ip and in which the noise components superimposed as a result of the digital computation in the PID computation section 61 have been attenuated. Therefore, even in the case where the sampling rate of the pump current Ip (digital signal) is increased, an increase in the level of the differential noise component of in the pump current Ip can be suppressed.

The second filter section 65 digitally extracts a gas detection signal S2 (second filter signal S2) from the digital signal representing the DAC control signal S1, extracted by the first filter section 63, such that components of the digital signal whose frequencies are higher than a predetermined second cut-off frequency (50 Hz in the present embodiment) are attenuated.

Since the gas detection signal S2 is a signal obtained from the DAC control signal S1 such that components (noise components) whose frequencies are higher than the second cut-off frequency are attenuated, the gas detection signal S2 is a digital signal in which the noise components (noise components superimposed as a result of the digital computation in the PID computation section 61) have been further attenuated or removed from the DAC control signal S1.

Since the DAC control signal S1 is smaller in the number of times of filter processing as compared with the gas detection signal S2, the DAC control signal S1 is a digital signal which represents the supply control current Tip for the pump current Ip and which reflects, to a relatively great extent, the latest change in the electromotive force of the electromotive force cell 24. Such a digital signal is suitable for feedback control of the pump cell 14. Therefore, by supplying to the pump cell 14 the pump current Ip generated on the basis of the DAC control signal S1, the pumping (pumping out and pumping in) of oxygen by the pump cell 14 can be performed properly in accordance with the latest change in the electromotive force of the electromotive force cell 24.

Notably, the first filter section 63 sends to the current DA conversion section 35 the DAC control signal S1 extracted from the digital signal representing the supply control current Tip. The DAC control signal S1 is a digital signal which contains information regarding the current value and supply direction (forward direction or reverse direction) of the supply control value for the pump current Ip.

As described above, the current DA conversion section 35 having received the DAC control signal S1 converts the received digital signal (digital information) to an analog signal (i.e., performs DA conversion) and supplies to the pump cell 14 a pump current determined on the basis of the DAC control signal S1.

Since the gas detection signal S2 is larger in the number of times of filter processing as compared with the DAC control signal S1, the gas detection signal S2 is a digital signal which represents the supply control current Tip for the pump current Ip and which reflects, to a relatively great extent, a change in the electromotive force of the electromotive force cell 24 over a long period of time. Such a digital signal is suitable for detection of a particular component (oxygen) contained in the object gas (exhaust gas).

Therefore, by using the gas detection signal S2 as a signal for detecting the concentration of oxygen contained in exhaust gas, it becomes possible to detect the concentration of oxygen contained in exhaust gas on the basis of a change in the electromotive force of the electromotive force cell 24 over a long period of time. As a result, the oxygen concentration detection accuracy can be improved.

Notably, the second filter section 65 sends the gas detection signal S2 extracted from the DAC control signal S1 to the gas concentration computation section 37. The gas detection signal S2 is a digital signal which contains information regarding the current value and supply direction (forward direction or reverse direction) of the supply control value for the pump current Ip.

As described above, the gas concentration computation section 37 having received the gas detection signal S2 computes the concentration of a particular gas (oxygen in the present embodiment) contained in exhaust gas on the basis of the gas detection signal S2 which contains the information of the supply control value for the pump current Ip computed in the digital computation section 33.

In the sensor control apparatus 2, the first cut-off frequency of the first filter section 63 is higher than the second cut-off frequency of the second filter section 65.

In this case, the DAC control signal S1 (the first filter signal) becomes a digital signal which contains components within a wider frequency range as compared with the gas detection signal S2 (the second filter signal) and becomes a digital signal which represents the supply control current Tip for the pump current Ip and which reflects, to a relatively great extent, the latest change in the electromotive force of the electromotive force cell 24.

Therefore, by supplying to the pump cell 14 the pump current Ip generated on the basis of the DAC control signal S1, the pumping of oxygen by the pump cell 14 can be performed properly in accordance with the latest change in the electromotive force of the electromotive force cell 24.

Also, the gas detection signal S2 becomes a digital signal which contains components within a narrower frequency range as compared with the DAC control signal S1 and becomes a digital signal which represents the supply control current Tip for the pump current Ip and which reflects, to a relatively great extent, a change in the electromotive force of the electromotive force cell 24 over a long period of time.

Therefore, by using the gas detection signal S2 as a signal for detecting the concentration of oxygen contained in exhaust gas, the concentration of oxygen contained in exhaust gas can be detected on the basis of a change in the electromotive force of the electromotive force cell 24 over a long period of time. As a result, the oxygen concentration detection accuracy can be improved.

1-4. Effects

As described above, in the gas detection system 1 of the present embodiment, the sensor control apparatus 2 includes the multiplexer 50, the AD conversion section 31, the digital computation section 33, and the current DA conversion section 35.

As described above, the digital computation section 33 at the time when it executes the pump current control processing includes the PID computation section 61, the first filter section 63, and the second filter section 65 as functional sections.

The PID computation section 61 performs PID computation on the basis of the deviation ΔVs between the target control voltage and the detection voltage Vs of the electromotive force cell 24 (the electromotive force of the electromotive force cell 24), and computes the supply control value (supply control current Tip) for the pump current Ip supplied to the pump cell 14 such that the deviation ΔVs approaches 0 (in other words, the detection voltage Vs approaches the target control voltage).

The first filter section 63 digitally extracts the DAC control signal S1 (the first filter signal S1) from a digital signal representing the supply control current Tip computed by the PID computation section 61. The DAC control signal S1 is a digital signal which represents the supply control current Tip for the pump current Ip and in which the noise components superimposed as a result of the digital computation in the PID computation section 61 have been attenuated. Therefore, even in the case where the sampling rate of the pump current Ip (digital signal) is increased, an increase in the level of the differential noise component of the pump current Ip can be suppressed.

The second filter section 65 digitally extracts the gas detection signal S2 (the second filter signal S2) from a digital signal representing the DAC control signal S1 extracted by the first filter section 63. The gas detection signal S2 is a digital signal in which the noise components (noise components superimposed as a result of the digital computation in the PID computation section 61) have been further attenuated or removed from the DAC control signal S1.

Since the DAC control signal S1 is smaller in the number of times of filter processing as compared with the gas detection signal S2, the DAC control signal S1 is a digital signal which represents the supply control current Tip for the pump current Ip and which reflects, to a relatively great extent, the latest change in the electromotive force of the electromotive force cell 24. Such a digital signal is suitable for feedback control of the pump cell 14.

Therefore, by supplying to the pump cell 14 the pump current Ip generated on the basis of the DAC control signal S1, the pumping (pumping out and pumping in) of oxygen by the pump cell 14 can be performed properly in accordance with the latest change in the electromotive force of the electromotive force cell 24.

Since the gas detection signal S2 is larger in the number of times of filter processing as compared with the DAC control signal S1, the gas detection signal S2 is a digital signal which represents the supply control current Tip for the pump current Ip and which reflects, to a relatively great extent, a change in the electromotive force of the electromotive force cell 24 over a long period of time. Such a digital signal is suitable for detection of a particular component (oxygen) contained in the object gas (exhaust gas).

Therefore, by using the gas detection signal S2 as a signal for detecting the concentration of oxygen contained in exhaust gas, it becomes possible to detect the concentration of oxygen contained in exhaust gas on the basis of a change in the electromotive force of the electromotive force cell 24 over a long period of time. As a result, the oxygen concentration detection accuracy can be improved.

Therefore, according to the sensor control apparatus 2, even when the sampling rate of the pump current Ip (digital signal) is increased, an increase in the level of the differential noise component of the pump current Ip can be suppressed. Also, according to the sensor control apparatus 2, pumping (pumping out and pumping in) of oxygen by the pump cell 14 can be performed properly, and the accuracy in detecting the concentration of a particular component (oxygen) contained in the object gas (exhaust gas) can be improved.

1-5. Correspondence Between Embodiment and Claims

A description will be given of the correspondence between terms used in claims and terms used in the present embodiment.

The electromotive force cell 24 is an example of the detection cell; the pump cell 14 is an example of the oxygen pump cell; the gas sensor 8 is an example of the gas sensor; and the sensor control apparatus 2 is an example of the sensor control apparatus. The Vs+ terminal and the common terminal COM of the electromotive force cell 24 are an example of the two electrode terminals of the detection cell; and the Ip+ terminal and the common terminal COM of the pump cell 14 are an example of the two electrode terminals of the oxygen pump cell.

The multiplexer 50 is an example of the multiplexer; the AD conversion section 31 is an example of the analog-to-digital conversion section; the PID computation section 61 of the digital computation section 33 is an example of the supply control value computation section; and the current DA conversion section 35 is an example of the digital-to-analog conversion section.

Signal 1 is an example of the high occurrence-frequency signal; signals 2, 3, and 4 are an example of the low occurrence-frequency signal; one cycle which is the period of output of "signal 1, signal 2, signal 1, signal 3, signal 1, signal 4" is an example of the all signal output period.

The first filter section 63 of the digital computation section 33 is an example of the first filter section; the DAC control signal S1 is an example of the first filter signal; the second filter section 65 of the digital computation section 33 is an example of the second filter section; the gas detection signal S2 is an example of the second filter signal; and the gas detection system 1 is an example of the gas detection system.

B. Other Embodiments

Although an embodiment of the present invention have been described, the present invention is not limited to the above-described embodiment, and the present invention can be implemented in various forms without departing from the technical scope of the present invention.

For example, the number of analog signals input to the multiplexer is not limited to 4 and may be any number equal to or greater than 3. The multiplexer may be any multiplexer so long as it can output a plurality of input analog signals while classifying them into the high occurrence-frequency signal and the low occurrence-frequency signal.

The first cut-off frequency of the first filter section and the second cut-off frequency of the second filter section are not limited to the above-described frequencies. Also, the first cut-off frequency of the first filter section is not limited to frequencies higher than the second cut-off frequency of the second filter section, and the first cut-off frequency may be the same as the second cut-off frequency.

Also, the present invention is not limited to a gas detection system and a sensor control apparatus which are used for the purpose of detecting a particular gas contained in exhaust gas discharged from an internal combustion engine, and may be used for the purpose of detecting a particular gas (e.g., oxygen) contained in intake gas introduced into an internal combustion engine or for the purpose of detecting a particular gas (e.g., oxygen) contained in an environmental gas.

DESCRIPTION OF REFERENCE NUMERALS AND SYMBOLS

1: gas detection system
2: sensor control apparatus
8: gas sensor
14: pump cell
24: electromotive force cell
31: analog-to-digital conversion section (AD conversion section)
33: digital computation section
35: current digital-to-analog conversion section (current DA conversion section)
37: gas concentration computation section
46: operational amplifier
48: reference voltage generation section
50: multiplexer
61: PID computation section
63: first filter section
65: second filter section
COM: common terminal
GND: ground potential
S1: DAC control signal
S2: gas detection signal.

What is claimed is:

1. A sensor control apparatus for controlling a gas sensor including a detection cell which produces an electromotive force corresponding to a particular component contained in an object gas and an oxygen pump cell which performs pumping in or pumping out of oxygen in accordance with a pump current supplied to the oxygen pump cell, the sensor control apparatus comprising:
an analog-to-digital conversion section configured to convert an analog signal representing the electromotive force of the detection cell to a digital value of the electromotive force;
a supply control value computation section configured to digitally compute a supply control value for the pump current supplied to the oxygen pump cell on the basis of the digital value of the electromotive force;
a first filter section configured to digitally extract a first filter signal from a digital signal representing the supply control value for the pump current such that components of the digital signal whose frequencies are higher than a predetermined first cut-off frequency are attenuated;
a second filter section configured to digitally extract a second filter signal from the first filter signal such that components of the first filter signal whose frequencies are higher than a predetermined second cut-off frequency are attenuated; and
a digital-to-analog conversion section configured to generate the pump current supplied to the oxygen pump cell on the basis of the first filter signal;
wherein the second filter section outputs to an external apparatus the second filter signal as a pump current signal for detection of the particular component contained in the object gas.

2. The sensor control apparatus according to claim 1, wherein the first cut-off frequency is higher than the second cut-off frequency.

3. A gas detection system comprising:
a gas sensor including a detection cell which produces an electromotive force corresponding to a particular component contained in an object gas and an oxygen pump cell which performs pumping in or pumping out of oxygen in accordance with a pump current supplied to the oxygen pump cell; and
a sensor control apparatus for controlling the gas sensor, the sensor control apparatus including
an analog-to-digital conversion section configured to convert an analog signal representing the electromotive force of the detection cell to a digital value of the electromotive force,
a supply control value computation section configured to digitally compute a supply control value for the pump current supplied to the oxygen pump cell on the basis of the digital value of the electromotive force,
a first filter section configured to digitally extract a first filter signal from a digital signal representing the supply control value for the pump current such that components of the digital signal whose frequencies are higher than a predetermined first cut-off frequency are attenuated,
a second filter section configured to digitally extract a second filter signal from the first filter signal such that components of the first filter signal whose frequencies are higher than a predetermined second cut-off frequency are attenuated, and
a digital-to-analog conversion section configured to generate the pump current supplied to the oxygen pump cell on the basis of the first filter signal;
wherein the second filter section outputs to an external apparatus the second filter signal as a pump current signal for detection of the particular component contained in the object gas.

4. The sensor control apparatus of claim 3, wherein the first cut-off frequency is higher than the second cut-off frequency.

* * * * *